US008095192B2

(12) United States Patent
Baker, Jr. et al.

(10) Patent No.: US 8,095,192 B2
(45) Date of Patent: Jan. 10, 2012

(54) SIGNAL QUALITY METRICS DESIGN FOR QUALIFYING DATA FOR A PHYSIOLOGICAL MONITOR

(75) Inventors: Clark R. Baker, Jr., Castro Valley, CA (US); Edward M. Richards, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1621 days.

(21) Appl. No.: 11/293,714

(22) Filed: Dec. 2, 2005

(65) Prior Publication Data

US 2006/0135860 A1 Jun. 22, 2006

Related U.S. Application Data

(63) Continuation of application No. 10/341,318, filed on Jan. 10, 2003, now Pat. No. 7,006,856.

(51) Int. Cl.
*A61B 5/1455* (2006.01)
*A61B 5/02* (2006.01)

(52) U.S. Cl. ......... 600/310; 600/322; 600/323; 600/502

(58) Field of Classification Search .................. 600/310, 600/323, 330–331, 336, 338, 322, 324, 334, 600/335
See application file for complete search history.

(56) References Cited

U.S. PATENT DOCUMENTS

| | | | |
|---|---|---|---|
| 3,638,640 A | | 2/1972 | Shaw |
| 4,533,346 A | * | 8/1985 | Cosgrove et al. ............... 604/66 |
| 4,653,498 A | | 3/1987 | New, Jr. et al. |
| 4,714,341 A | | 12/1987 | Hamaguri et al. |
| 4,776,339 A | * | 10/1988 | Schreiber ...................... 600/324 |
| 4,805,623 A | | 2/1989 | Jöbsis |
| 4,807,631 A | | 2/1989 | Hersh et al. |
| 4,858,615 A | | 8/1989 | Meinema |
| 4,863,265 A | | 9/1989 | Flower et al. |
| 4,911,167 A | | 3/1990 | Corenman et al. |
| 4,913,150 A | | 4/1990 | Cheung et al. |

(Continued)

FOREIGN PATENT DOCUMENTS

DE 19640807 9/1997

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
*Assistant Examiner* — Chu Chuan (JJ) Liu (57) ABSTRACT

The present disclosure generally relates to determining the quality of signal used for measuring a physiological parameter. One embodiment of the present disclosure is directed towards a pulse oximeter, where the measured physiological parameter includes a patient's pulse rate and blood oxygen saturation. The signal quality is calculated by combining a plurality of signal quality indicators, each of which is an indicator of a quality of the measured signal. The value of the signal quality metric is compared to a threshold and based on this comparison various decisions are made by the medical device. One decision is directed towards deciding whether or not to display the measured physiological parameter, to ensure that only accurate measured values are displayed. Another decision is directed towards providing feedback to guide the clinician to adjust the location of the sensor to a more suitable tissue location.

27 Claims, 2 Drawing Sheets

U.S. PATENT DOCUMENTS

| | | | |
|---|---|---|---|
| 4,936,679 A | 6/1990 | Mersch | |
| 4,938,218 A | 7/1990 | Goodman et al. | |
| 4,942,877 A | 7/1990 | Sakai et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,503,148 A | 4/1996 | Pologe et al. | |
| 5,529,064 A | 6/1996 | Rall et al. | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Keunstner | |
| 5,724,983 A * | 3/1998 | Selker et al. | 600/301 |
| 5,730,124 A | 3/1998 | Yamauchi | |
| 5,758,644 A | 6/1998 | Diab et al. | |
| 5,779,631 A | 7/1998 | Chance | |
| 5,782,755 A * | 7/1998 | Chance et al. | 600/322 |
| 5,782,757 A | 7/1998 | Diab et al. | |
| 5,782,758 A | 7/1998 | Ausec et al. | |
| 5,786,592 A | 7/1998 | Hök | |
| 5,817,027 A | 10/1998 | Arand et al. | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,846,190 A | 12/1998 | Woehrle | |
| 5,865,736 A | 2/1999 | Baker, Jr. et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,924,980 A | 7/1999 | Coetzee | |
| 5,934,277 A | 8/1999 | Mortz | |
| 5,987,343 A | 11/1999 | Kinast | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,035,223 A | 3/2000 | Baker, Jr. | |
| 6,064,898 A | 5/2000 | Aldrich | |
| 6,081,742 A | 6/2000 | Amano et al. | |
| 6,088,607 A | 7/2000 | Diab et al. | |
| 6,104,938 A | 8/2000 | Huiku et al. | |
| 6,120,460 A | 9/2000 | Abreu | |
| 6,134,460 A | 10/2000 | Chance | |
| 6,135,952 A | 10/2000 | Coetzee | |
| 6,150,951 A | 11/2000 | Olejniczak | |
| 6,154,667 A | 11/2000 | Miura et al. | |
| 6,163,715 A | 12/2000 | Larsen et al. | |
| 6,178,343 B1 | 1/2001 | Bindszus et al. | |
| 6,181,958 B1 | 1/2001 | Steuer et al. | |
| 6,181,959 B1 | 1/2001 | Schöllermann et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,358,213 B1 | 3/2002 | Friedman et al. | |
| 6,360,114 B1 | 3/2002 | Diab et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,449,501 B1 | 9/2002 | Reuss | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,510,329 B2 * | 1/2003 | Heckel | 600/310 |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,675,031 B1 | 1/2004 | Porges et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,725,074 B1 | 4/2004 | Kastle | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,801,802 B2 | 10/2004 | Sitzman et al. | |
| 6,829,496 B2 | 12/2004 | Nagai et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,127,278 B2 | 10/2006 | Melker et al. | |
| 7,162,306 B2 | 1/2007 | Caby et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,373,193 B2 | 5/2008 | Al-Ali et al. | |

| | | | |
|---|---|---|---|
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035315 A1* | 3/2002 | Ali et al. | 600/300 |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0072660 A1* | 6/2002 | Diab et al. | 600/323 |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0187337 A1 | 10/2003 | Tarassenko et al. | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0087846 A1 | 5/2004 | Wasserman | |
| 2004/0097797 A1 | 5/2004 | Porges et al. | |
| 2004/0107065 A1 | 6/2004 | Al-Ali | |
| 2004/0127779 A1 | 7/2004 | Steuer et al. | |
| 2004/0133087 A1 | 7/2004 | Ali et al. | |
| 2004/0158134 A1 | 8/2004 | Diab et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0204865 A1 | 10/2004 | Lee et al. | |
| 2004/0210146 A1 | 10/2004 | Diab et al. | |
| 2004/0230106 A1 | 11/2004 | Schmitt et al. | |
| 2005/0033128 A1 | 2/2005 | Ali et al. | |
| 2005/0080323 A1 | 4/2005 | Kato | |
| 2005/0101850 A1 | 5/2005 | Parker | |
| 2005/0113651 A1 | 5/2005 | Wood et al. | |
| 2005/0113656 A1 | 5/2005 | Chance | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0267346 A1 | 12/2005 | Faber et al. | |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0030764 A1 | 2/2006 | Porges et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |

FOREIGN PATENT DOCUMENTS

| | | |
|---|---|---|
| EP | 0 221 357 A2 | 5/1987 |
| EP | 0 571 225 A2 | 11/1993 |
| EP | 0 571 225 A3 | 11/1993 |
| EP | 0630203 | 12/1994 |
| EP | 1491135 | 12/2004 |
| JP | 2237544 | 9/1990 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 9192120 | 7/1997 |
| JP | 10216115 | 8/1998 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| JP | 3939782 | 7/2007 |
| WO | WO9101678 | 2/1991 |
| WO | WO9221281 | 12/1992 |
| WO | WO9309711 | 5/1993 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO 00/61000 A1 | 10/2000 |
| WO | WO2005009221 | 2/2005 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

R. Neumann, et al.; "Fourier Artifact suppression Technology Provides Reliable $SpO_2$," *Abstracts*, A11, p. S105. (undated).

\* cited by examiner

SIGNAL QUALITY METRICS DESIGN FOR QUALIFYING DATA FOR A PHYSIOLOGICAL MONITOR

CROSS-REFERENCE TO RELATED APPLICATIONS

This application is a Continuation of U.S. application Ser. No. 10/341,318, filed Jan. 10, 2003, the disclosure of which is hereby incorporated by reference.

BACKGROUND OF THE INVENTION

The present invention relates to physiological monitoring equipment and, in particular, monitoring equipment that include processes for quantitatively estimating the quality of the detected signals corresponding to physiological measurements and which provide appropriate feedback to the clinician based on that estimate of signal quality.

Typically, for physiological monitoring instruments, the instrument is unable to accurately determine the accuracy and reliability, or a quality of a signal obtained from the sensor. An example of such physiological monitoring instrument is a pulse oximeter. Pulse oximetry is typically used to measure various blood characteristics including the blood oxygen saturation of hemoglobin in arterial blood and the pulse rate of the patient.

Measurement of these characteristics has been accomplished by use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical measurement is the familiar plethysmographic waveform due to cyclic light attenuation.

The accuracy of the estimates of the blood flow characteristics depends on a number of factors. For example, the light absorption characteristics typically vary from patient to patient depending on their physiology. Moreover, the absorption characteristics vary depending on the location (e.g., the foot, finger, ear, and so on) where the sensor is applied, and whether there are objects interfering between the sensor and the tissue location (e.g., hair, nail polish, etc.). Further, the light absorption characteristics vary depending on the design or model of the sensor. Also, the light absorption characteristics of any single sensor design vary from sensor to sensor (e.g., due to different characteristics of the light sources or photo-detector, or both). The clinician applying the sensor correctly or incorrectly may also have a large impact in the results, for example, by loosely or firmly applying the sensor or by applying the sensor to a body part which is inappropriate for the particular sensor design being used.

The clinician needs to know how accurate or reliable of a reading is being provided by the instrument. Moreover, the instrument should ideally provide measurements that are accurate and reliable. A measure of the reliability and accuracy of a physiological measurement can be the quality of the signal. Although quality is a rather nebulous term, generally speaking, high quality signals are indicative of more reliable and more accurate physiological measurements and conversely, low quality signals are indicative of less reliable and accurate signals.

Some oximeters devices qualify measurements before displaying them on the monitor, by comparing the measured signals to various phenomenologically-derived criteria. These oximeters qualify the signal by making an assessment of its accuracy and only display values of estimated parameters when the signal quality meets certain criteria. The disadvantage of such approaches is that no feedback is provided to the clinician regarding what the clinician should do to improve the measurements. Worse yet, if the signal quality is deemed poor, and a decision is made by the device to not display the measured value, then the clinician is left with no more information than if the device was never used in the first place, which can be frustrating. Most typically, the clinician will end up removing the sensor from a particular tissue location to re-attach it to another location and heuristically repeats this process until more reliable measurements, deemed worthy of being displayed are provided by the instrument. The time duration where a measured value is displayed is known as the posting time. An ideal oximeter provides both accurate measurements and high posting times. While some instruments make estimates of signal quality, there still exists a need for improvements in this area; improvements that assess the quality of the signal while maintaining or increasing the posting times of the measured values. There is therefore a need for an improved and more quantitative assessment of signal quality. There is also a need for the monitoring equipment to guide the clinician to make necessary adjustments to improve the signal quality.

The issues related to obtaining high quality signals which are indicative of reliable and accurate measurements of critical physiological parameters, are further compounded when the sensor is "blindly" placed. A blindly placed sensor is one that is placed adjacent to a tissue location that is not readily observable by the clinician. An example of such a blind sensor placement is when a clinician uses a fetal pulse oximeter. The fetal pulse oximetry sensor is placed through the cervix during labor. The sensor, which is supposed to lie between the cheek of the fetus and the wall of the uterus, measures the fetus' blood oxygen levels. The sensor is connected to a monitor that displays the fetus' current blood oxygen levels. During the course of monitoring the quality of the signal obtained can vary significantly and rapidly. This change in the quality of the signal can be caused by sensor-to-fetus positioning irrespective of actual fetus physiological condition, resulting in spurious readings and interrupted posting times over relatively short time frames. Monitoring the heart rate of the fetus is an indirect way of assessing the amount of oxygen in the fetus' blood, which allows a clinician to determine whether the fetus is in distress during labor. Knowing the fetus' blood oxygen level during labor, and hence whether the fetus is in distress or not, allows a clinician to better decide as to whether to perform a cesarean versus letting the labor progress. Therefore, with a blindly placed sensor, and especially one used in a fetal pulse oximetry, the need for an improved assessment of signal quality is heightened. Moreover, just as in non-blindly placed sensors, there is also a need for the medical device to provide guidance to a clinician to improve the quality of the signal when the signal quality is so low as to indicate an inaccurate and/or unreliable estimate of a measured value.

BRIEF SUMMARY OF THE INVENTION

The present invention provides a method and a device for determining the quality of signal used for measuring a physiological parameter. One embodiment of the present invention is directed towards a pulse oximeter, where the measured physiological parameter includes a patient's pulse rate and blood oxygen saturation. The signal quality, which is indicative of the accuracy and reliability of the measured physiological parameter, is calculated by combining a plurality of signal quality indicators, each of which is an indicator of a quality of the measured signal. The value of the signal quality metric is compared to a threshold and based on this comparison various decisions are made by the medical device. One decision is directed towards deciding whether or not to display the measured physiological parameter, to ensure that only accurate measured values are displayed. Another decision is directed towards providing feedback to guide the clinician to adjust the location of the sensor to a more suitable tissue location.

In a pulse oximeter embodiment, the signal quality indicators of the present invention include: a signal measure indicative of the degree of similarity of an infrared and red waveforms; a signal measure indicative of a low light level; a signal measure indicative of an arterial pulse shape; a signal measure indicative of the high frequency signal component in the measure value; a signal measure indicative of a consistency of a pulse shape; a signal measure indicative of an arterial pulse amplitude; a signal measure indicative of modulation ratios of red to infrared modulations and a signal measure indicative of a period of an arterial pulse. These various indicators provide for an indirect assessments of the presence of known error sources in pulse oximetry measurements, which include optical interference between the sensor and the tissue location; light modulation by other than the patient's pulsatile tissue bed; physical movement of the patient and improper tissue-to-sensor positioning.

The signal quality is calculated periodically, and hence can vary significantly and rapidly. In order to temper the decision making algorithm's response to changes in the calculated signal quality, certain embodiments of the present invention base the decisions to display a measured value and/or the decisions to guide the clinician, by comparing a PID-processed (proportional, integral and derivative) signal quality value to a threshold. PID processing is known in the controls arena and provides several advantages. In the context of a medical device and specifically a pulse oximeter device, the use of PID processing will ensure that a small magnitude, short time change in signal quality signal is reacted to quickly, preventing spurious responses, or delayed responses that could result in the display of inaccurate information. Further, a large magnitude signal quality change is responded to in a shorter period of time, and a slower long term change in signal quality is responded to in an adequate time frame to give the clinician sufficient timely information to work with.

For a further understanding of the nature and advantages of the invention, reference should be made to the following description taken in conjunction with the accompanying drawings.

DETAILED DESCRIPTION OF THE INVENTION

Embodiments of the present invention describe a physiological monitor and sensor incorporating methods and systems that quantitatively estimate signal quality, and based on that estimate of signal quality decide whether to display the measured physiologic parameter and/or provide feedback to guide the clinician to adjust the location of the sensor. The signal quality estimate is based on the measurement of a plurality of signal quality indicators which when combined provide a quantitative measure of signal quality.

The invention is particularly applicable to and will be explained by reference to measurements of oxygen saturation of hemoglobin in arterial blood and patient hear rate, as in pulse oximeter monitors and pulse oximetry sensors. However, it should be realized the invention is equally applicable to any generalized patient monitor and associated patient sensor, such as ECG, blood pressure, temperature, etc., and is not limited to use only with oximetry or pulse oximetry. A brief description of pulse oximeters is provided below.

Pulse Oximeters

As described above, pulse oximeters are typically used to measure various blood flow characteristics including the blood oxygen saturation of hemoglobin in arterial blood and the heartbeat of a patient. Measurement of these characteristics has been accomplished by the use of a non-invasive sensor that passes light through a portion of a patient's blood perfused tissue and photo-electrically senses the absorption and scattering of light in such tissue.

The light passed through the tissue is typically selected to be of two or more wavelengths that are absorbed by the blood in an amount related to the amount of blood constituent present in the blood. The amount of transmitted light that passes through the tissue varies in accordance with the changing amount of blood constituent in the tissue and the related light absorption.

To estimate arterial blood oxygen saturation of a patient, conventional two-wavelength pulse oximeters emit light from two light emitting diodes (LEDs) into a pulsatile tissue bed and collect the transmitted light with a photo detector positioned on an opposite surface (i.e., for transmission pulse oximetry) or an adjacent surface (i.e., for reflectance pulse oximetry). The LEDs and photodetector are typically housed in a reusable or disposable oximeter sensor that couples to a pulse oximeter electronics and display unit. One of the two LEDs' primary wavelength is selected at a point in the electromagnetic spectrum where the absorption of oxyhemoglobin ($HbO_2$) differs from the absorption of reduced hemoglobin (Hb). The second of the two LEDs' wavelength is selected at a different point in the spectrum where the absorption of Hb and $HbO_2$ differs from those at the first wavelength. Commercial pulse oximeters typically utilize one wavelength in the near red part of the visible spectrum near 660 nanometers (nm) and one in the near infrared (IR) part of the spectrum in the range of 880-940 nm.

Figure 1:
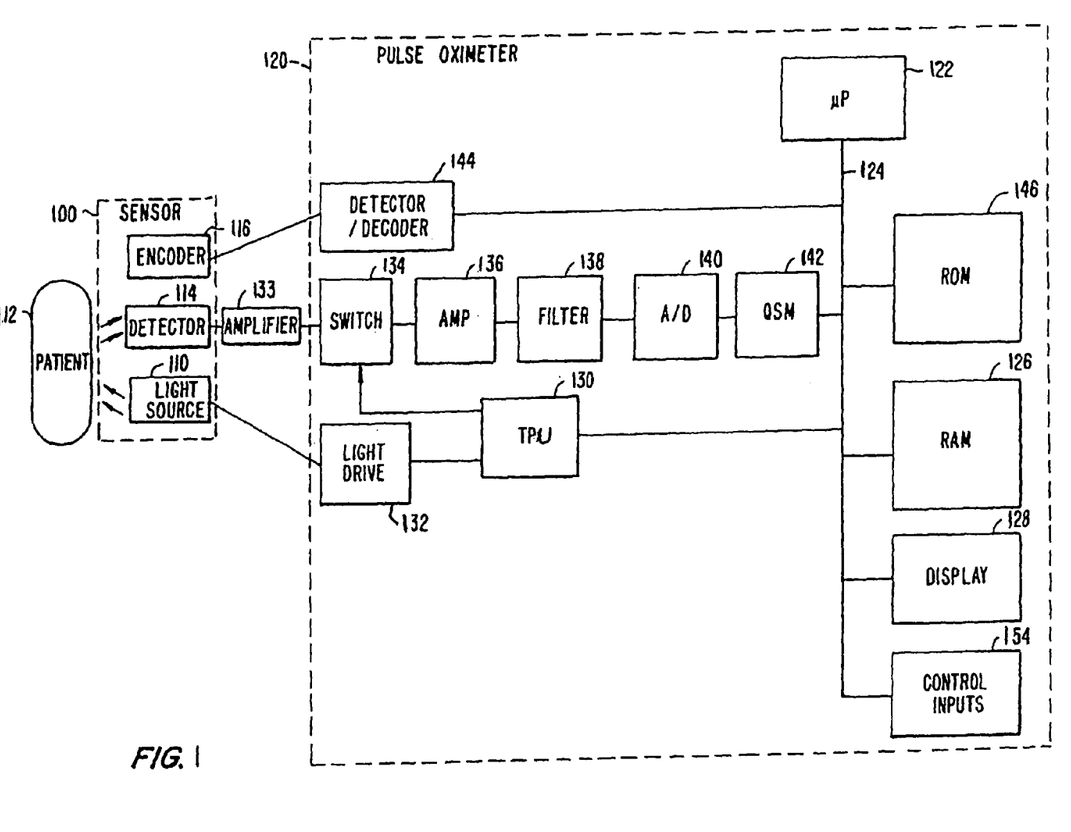
FIG. 1 is a block diagram of an exemplary oximeter.

FIG. 1 is a block diagram of one embodiment of a pulse oximeter that may be configured to implement the embodiments of the present invention. The filter embodiments of the present invention can be a data processing algorithm that is executed by the microprocessor 122, described below. Light from light source 110 passes into patient tissue 112, and is scattered and detected by photodetector 114. A sensor 100 containing the light source and photodetector may also contain an encoder 116 which provides signals indicative of the wavelength of light source 110 to allow the oximeter to select appropriate calibration coefficients for calculating oxygen saturation. Encoder 116 may, for instance, be a resistor.

Sensor 100 is connected to a pulse oximeter 120. The oximeter includes a microprocessor 122 connected to an internal bus 124. Also connected to the bus is a RAM memory 126 and a display 128. A time processing unit (TPU) 130 provides timing control signals to light drive circuitry 132 which controls when light source 110 is illuminated, and if multiple light sources are used, the multiplexed timing for the different light sources. TPU 130 also controls the gating-in of signals from photodetector 114 through an amplifier 133 and a switching circuit 134. These signals are sampled at the proper time, depending upon which of multiple light sources is illuminated, if multiple light sources are used. The received signal is passed through an amplifier 136, a low pass filter 138, and an analog-to-digital converter 140. The digital data is then stored in a queued serial module (QSM) 142, for later downloading to RAM 126 as QSM 142 fills up. In one embodiment, there may be multiple parallel paths of separate amplifier filter and A/D converters for multiple light wavelengths or spectrums received.

Based on the value of the received signals corresponding to the light received by photodetector 114, microprocessor 122 will calculate the oxygen saturation using various algorithms. These algorithms require coefficients, which may be empirically determined, corresponding to, for example, the wavelengths of light used. These are stored in a ROM 146. The particular set of coefficients chosen for any pair of wavelength spectrums is determined by the value indicated by encoder 116 corresponding to a particular light source in a particular sensor 100. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore any number of methods or algorithms may be used to determine a patient's pulse rate, oxygen saturation or any other desired physiological parameter. The pulse oximeter shown in FIG. 1 is shown for exemplary purposes and is not meant to limit the embodiments of the present invention. For example, the sensor can be replaced by other appropriate sensors for use at other tissue locations including the ear, foot, forehead and nose of adult, infant, neonatal and perinatal patients.

Oxygen saturation can be estimated using various techniques. In one common technique, the photo-current generated by the photo-detector is conditioned and processed to determine the modulation ratio of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios or ratio of ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. An electronic processor for calculating in vivo blood oxygenation levels using pulsed light is described in U.S. Pat. No. 5,348,004, entitled "ELECTRONIC PROCESSOR FOR PULSE OXIMETER," issued Sep. 20, 1994, and a display monitor for a pulse oximeter is described in U.S. Pat. No. 4,653,498, entitled "PULSE OXIMETER MONITOR," issued Mar. 31, 1987. All five patents are assigned to the assignee of the present invention and incorporated herein by reference.

The brief description of pulse oximeters, and associated electronic circuitry and algorithms described above serve as a contextual fabric for describing the method for estimating signal quality and the signal quality metrics design according to embodiments of the present invention, which are described below.

Signal Quality

While the methodologies described in the patents cited above are used to provide estimates of blood oxygen saturation and pulse rate, many intermediate signals are first obtained by the oximetry sensor which when finally processed through these circuits and algorithms conclude in determining these final estimates of blood oxygen saturation and pulse rate. A set of these intermediate signals is used for signal quality indicators. The signal quality indicators are then combined and processed to estimate a signal quality metric. The value of the signal quality metric is compared to a threshold and based on this comparison various decisions are made by the medical device. One decision is directed towards deciding whether or not to display the measured physiologic parameter. Another decision is directed towards providing feedback to guide the clinician to adjust the location of the sensor, when the signal quality metric is below a threshold.

A. Signal Quality Indicators

A signal quality indicator is a measured parameter that is capable of estimating the reliability and accuracy of a signal. For example, when measuring blood oxygen saturation using a pulse oximeter, a signal quality indicator is able to indirectly assess whether an estimate of a value of blood oxygen saturation is an accurate one. This determination of accuracy is made possible by a thorough and detailed study of volumes of measured values and various indicators to determine which indicators are indicative of signal quality and what, if any, is the correlation between the indicator and the accuracy of the estimated value. While a particular indicator may be highly correlated to the accuracy of a measured value, it is determined that a combination of several indicators correlates better to the accuracy of measured value over a wider range of clinical conditions. A few of these indicators are referred to as the "OVERLAP," "MIN-MAX-MIN," "PATH LENGTH" and "IR nAv" indicators. These, as well as other indicators and their utilities in determining the signal's quality and hence the accuracy of oxygen saturation estimates are each described below.

The "OVERLAP" indicator is a measure of the similarity of the pulse forms obtained from different wavelengths, such as for example, the infrared and red pulse forms. While many algorithms may be used to compute "OVERLAP," one equation that may be used to compute it is as follows:

$$R = \frac{\ln(Red_{max} / Red_{min})}{(IR_{max} / IR_{min})}$$

$$Overlap = \frac{\sum \min(IR_t - IR_{min}, (Red_t - Red_{min}) / R)}{\sum IR_t - IR_{min}}$$

where $IR_t$ and $Red_t$ have been AC—coupled and normalized by their respective DC levels and the summations cover a timespan ranging from one to several seconds. This indicator is useful in determining the accuracy of the measured oxygen saturation value because it provides for an indirect method of sensing the extent to which the two wavelengths which are used by a sensor are probing the same tissue volume. It is known that errors in oxygen saturation measurements using pulse oximeters occur when the two light sources providing light at two wavelengths probe two different tissue locations. Thus when the two or more different pulse forms do not look the same, it is likely that photons are being modulated by different volumes of tissue, which is known to cause inaccurate measurements. On the other hand, when the two or more pulse forms (e.g., infrared and red) look the same, or "OVERLAP," then this indicates that it is likely that the same tissue volume is being probed by the two different wavelengths of light, thus avoiding a known source of error.

The "MIN-MAX-MIN" indicator provides for a measure of the arterial pulse shape. The arterial pulse referred to herein is caused by a cardiac cycle commonly referred to a heartbeat. During a typical cardiac cycle, blood pressure rises from a minimum value (MIN) at diastole to a maximum (MAX) at systole. The "MIN-MAX-MIN" indicator is a ratio represented by a fraction having the time it takes the pulse to go from a MAX to a MIN as the numerator and having the time it takes the pulse to go from a MIN to a MAX as the denominator. This indicator provides an indication of the ratio of fall to rise times of arterial pulse. A fundamental fact of human physiology is that in a typical arterial pulse, it takes a shorter time to go from the diastole to systole (MIN to MAX) than it does to go from systole to diastole (MAX to MIN). Recognizing this fundamental physiological aspect, then if the "MIN-MAX-MIN" indicator shows that for a pulse, the rise time is bigger than the fall time, then this indicates that the sensor's light is being modulated by other than an arterial pulse. The inventors have identified that when a pulse's rise time is bigger than its fall time, the light is not modulated by pulsation of evenly distributed arterial blood, but it is most likely that the observed pulse-like phenomenon is due to throbbing of underlying large blood vessels or physical movement of the sensor. It is known that either of these mechanisms may cause large errors in the calibration of the resulting oxygen saturation estimate. Therefore, by analyzing the shape of the arterial pulse, the "MIN-MAX-MIN" indicator determines whether the light modulation is due to a pulsation, or evenly distributed arterial blood, or other phenomenon such as motion.

The "PATH LENGTH" indicator is also indicative of the pulse shape. This indicator provides for a measure of the frequency content of the pulse waveform relative to the pulse rate. While many algorithms may be used to compute "PATH LENGTH," one equation that may be used to compute it is as follows:

$$PathLength = \frac{\sum_{i=0}^{i=Samples\_in\_Pulse-1} |IR_{t-i} - IR_{t-i-1}|}{Pulse\_Max - Pulse\_Min}.$$

High values of this metric indicate that a high proportion of the energy in the pulse is at frequencies higher than the pulse rate. High frequency components in the arterial pulse shape are an indication that light is being modulated by other than arterial pulsations. These high frequency components are also most likely to be caused by movement of the sensor. As described above, it is known that physical movement is a source of error when estimating blood oxygen saturation in pulse oximeters. Therefore, the "PATH LENGTH" indicator, is also a motion indicator, which is used to infer that signals that have high frequency components often lead to inaccurate estimates of pulse rate and/or blood oxygen saturation.

The "IR nAv" indicator provides for an infrared (IR) measure of the optical density of the tissue. This indicator represents a light level which has been normalized for the LED's brightness. In other words, the "IR nAv" indicator is a low light level measure. It is recognized that the cause of a low light level measure is sensor misplacement, as in when a sensor is placed over hair or other medium interfering with the light path between the sensor and the probed tissue volume. Therefore, the "IR nAv" indicator is used to infer that the measured value is potentially inaccurate because of sensor misplacement.

In addition to the indicators described above, many other indicators also provide for estimates of signal quality and hence a measure of the accuracy of the physiological measurements. These include indicators that qualify: pulse shape; pulse amplitude; modulation ratios of the red to infrared signals, known as ratio of ratios and pulse period. Moreover, other indicators that trend the consistency of pulse shapes relative to each of these additional indicators are also viable as measures of signal quality.

The signal quality indicators described above, may be derived from any wavelength used by an oximeter. Further, these indicators may be derived after a variety of signal processing operations including filtering of the signal, such as low pass, high pass and comb filtering. Furthermore, although the indicators described above are based on time-domain analyses, similar indicators are derivable in the frequency domain as is apparent to those knowledgeable in signal processing.

B. Algorithms for Determining an Overall Signal Quality (SQ) Metric

As stated above, the signal quality indicators are processed and combined to provide an overall value for a lumped signal quality (SQ) metric. Many algorithms may be used to arrive at the lumped SQ value. An example of such an algorithm is shown below, which may be described as a combination of the "OVERLAP," "MIN-MAX-MIN" and "IR nAv" indicators.

$SQ=SQ1*(SQ2/100)*(SQ3/100)$, where

SQ1=100−5*(96−OVERLAP), clipped to between 0 and 100

SQ2=100−(MIN-MAX-MIN−16000)/70, clipped to between 0 and 100

SQ3=100−5*(25−IR nAv), clipped to between 50 and 100,

For example, for this particular algorithm, SQ is updated on each qualified pulse. Alternate algorithms update the calculation of SQ at other periodic rates, ranging from once every 5 seconds to once every one tenth of a second. The particular choice of algorithm which is used to compute an SQ, is very dependent on the choice of indicators and the target value for the lumped SQ parameter. As shown here, only three of the indicators are used, namely, "OVERLAP," "MIN-MAX-MIN" and "IR nAv." Using this particular algorithm, the SQ value is configured to have a range between 0 and 100. The algorithm shown above is for exemplary purposes only, since many other algorithms can be derived which would also combine various indicators to arrive at an overall signal quality metric. The advantage of this particular algorithm is that it is a relatively simple one, only using three signal quality indicators. Further, this particular algorithm processes the signal quality indicators by scaling and clipping the indicators to values to derive a signal quality metric which has a very ordinary range of between 0 and 100. Most, if not all practitioners in the technical and scientific communities can appreciate that a value of 100 represents a high quality value and that a value of 0 represents a low quality value. Depending on the choice of indicators and the desired range of values for the final SQ metric, many alternate algorithms can be contemplated, each having various different advantages and disadvantages as compared to the exemplary algorithm described above.

C. Processing SQ

Having determined a signal quality (SQ) value by combining various signal quality indicators, the next task in determining whether a measured value is accurate and worthy of being displayed on a pulse oximeter's monitor is to compare the SQ value to a threshold. As described above, the SQ value is calculated periodically, and therefore it can also change periodically. This change in signal quality can occur due to both changes in physiological conditions of the patient as well as non-physiologically induced changes. Non-physiological changes in signal quality can be caused by such factors as motion of the sensor, changes in the sensor to tissue positioning and optical interference between the sensor and the tissue location such as those caused by hair being placed in between the sensor and the tissue location. These non-physiological-based changes occur to a higher extent in perinatal pulse oximeters, where the sensor-to-fetus positioning can change rapidly as the fetus moves in the womb during the course of labor and delivery.

Algorithms that make the decision regarding whether or not to display a measured value of a physiological parameter on a display monitor of a pulse oximeter, must account for the potential rapid changes in signal quality. Thus, a small-magnitude, short-time change in signal quality should not be reacted to quickly, thus preventing annoying and spurious responses. On the other hand, small magnitude changes in signal quality should not cause a delayed response that could result in the display of inaccurate measurements. Therefore, to avoid erratic changes in the response of the diagnostic device, algorithms that decide whether or not a measured value is of a high enough quality, and algorithms that decide whether or not the value should be displayed preferably should act on a processed form of the SQ value.

The concept of tempering a system's response to on an input is known in the automatic controls arena. This concept is related to various operations, including the proportional (P), integral (I) and derivative (D) control operations, with each operation having different attributes. A control operation using a combination of proportional, integral and derivative operations in response to an input is referred to as a PID control system. The embodiments of the present invention enhance the algorithms which are used to make decisions regarding whether or not to display a measured value on a display monitor by incorporating PID operations with these algorithms. Each of the proportional, integral and derivative operations as applied to the SQ-based algorithms is described below.

With proportional control, a change in response is made which is proportional to the change in input. For example, with proportional control, if the decision to display a measured value depends on the SQ being equal to or above a threshold value, the instant the SQ value exceeds the threshold, the measured value is displayed, and the very instant the SQ value drops below the threshold, the measured value is removed from the display. While a proportional control operation may be instantly responsive, it will also respond erratically to erratic changes in input. This potential of an erratic response is not ideal because short-lived excursions in SQ will cause short-lived responses which are, as described above, not desired.

With integral control, the input change is integrated over time and a change in response occurs when an integrated threshold value is met. Consider, for example if the integral threshold for removing a measured value from a display is set to a value of 10 SQ-seconds, beyond a threshold of SQ of 80. Under this scenario, a drop in SQ from 81 to 79 would cause the displayed value to be removed in 5 seconds, since the deviation of 2 SQ (81−79=2 SQ) times 5 seconds would equal 10 SQ-seconds. A bigger drop in SQ beyond the threshold value would remove the displayed value sooner, and conversely a smaller drop in the SQ beyond the threshold would remove the displayed value later. Thus, an integral control operation delays the decision by waiting for an integrated threshold to be met. In this manner, an integral-based control operation is able to ride out short lived excursions and result in an overall smoother display operation for a pulse oximeter device.

Lastly, a derivative control system responds to the rate of change of the input parameter as opposed to the parameter itself, as in proportional control, or an integrated change in the parameter, as in integral control. A derivative-based system anticipates the change in the input parameter and is thus able to foresee when an increasing SQ value is nearing the SQ threshold. In other words, derivative control will cause a transition to display a measured value on the display monitor faster of SQ has improved over the last few sensing periods.

Thus, the diagnostic device's decision making directed to determining whether a measured value has a high enough SQ to be worthy of being displayed on an oximeter's monitor is based on comparing a PID processed SQ to a threshold value. The PID processed SQ value is achieved by operating on the SQ value using a combination of proportional, derivative and integral operations. For example, the decision to post may be made when the combination of the proportional, integral and derivative processed SQ value exceeds a threshold, as is shown below (i.e., display the measured value if P+I+D is greater than a threshold):

$P+I+D>$Threshold, where $P=P0*(SQ-75)/25$, where

P0 is a proportional component scalar;
SQ is signal quality $I=\int(SQ-50)dt$, where the integral is updated each second; and $D=D0*(SQ_1-SQ_0)/14$, where $SQ_1$ is the current signal quality
SQ0 is the signal quality one second before
D0 is the derivative component scalar Thus, various algorithms are used to compute a signal quality metric for comparison to a threshold. Further, before comparing the calculated SQ value, an alternate embodiment processes the SQ value using PID operations. Once the PID processed or non-processed SQ value is compared to a threshold, various decisions are made by the medical device. As stated above, one decision is directed towards deciding whether or not to display the measured physiologic parameter. Another decision is directed towards providing feedback to guide the clinician to adjust the location of the sensor, when the signal quality metric is below a threshold.

D. Decision Algorithm

Figure 2:
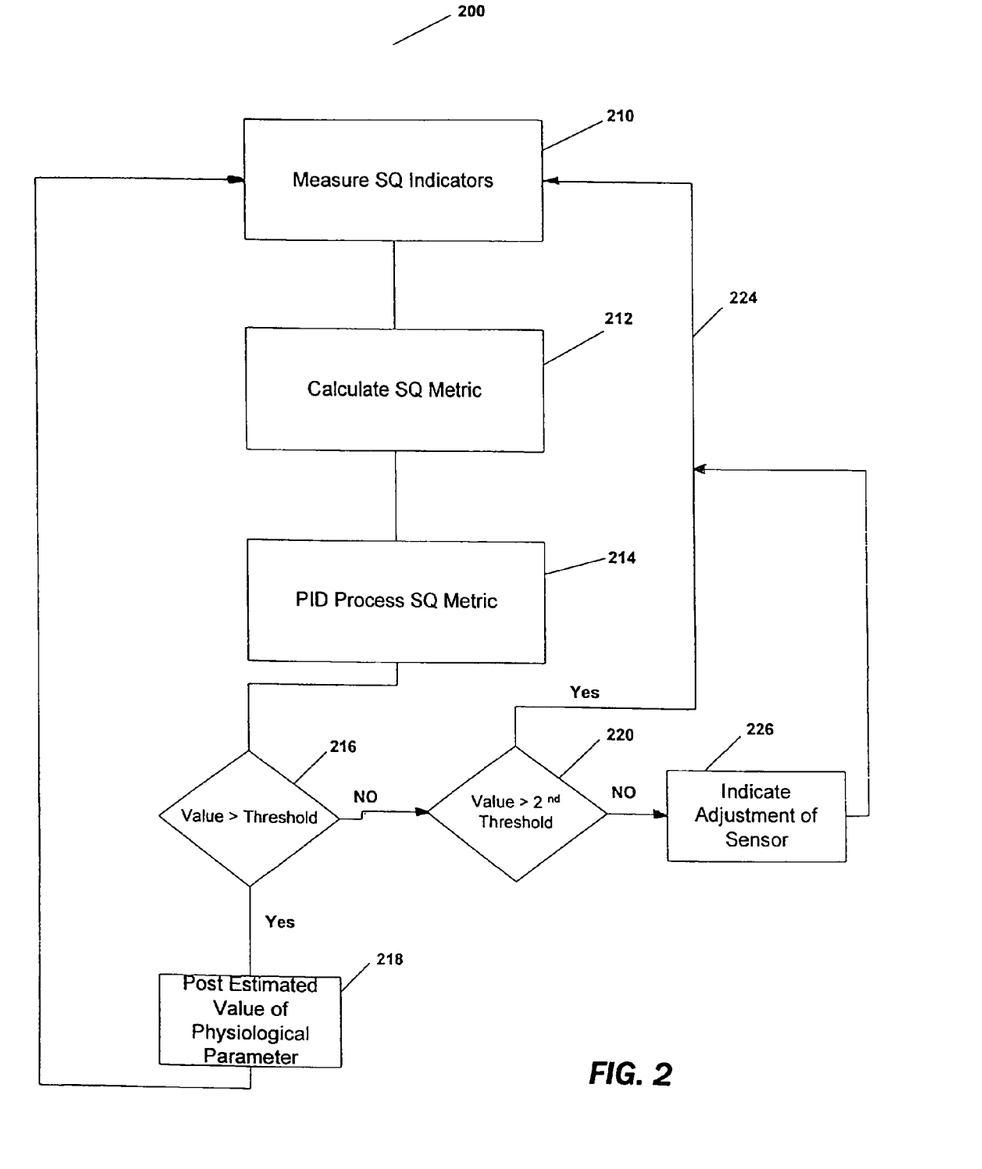
FIG. 2 is a flow chart showing an embodiment of the decision making algorithm of the present invention.

FIG. 2 is a flow chart 200 showing an embodiment of the above described decision making algorithm in accordance with the present invention. First a plurality of signal quality indicators are measured (step 210). Next, the signal quality indicators are processed and combined to calculate an SQ metric (step 212). As described above, the SQ value changes periodically, and may also change rapidly. To smooth out potential changes in the time-varying SQ value, it is PID processed (step 214). Next, the value of the PID processed SQ metric is compared to a threshold (step 216). If the value is at least equal to the threshold, the measured physiological value is sent to be displayed by the device's monitor (step 218). For example, when the medical device is a pulse oximeter with a display monitor and the device is measuring oxygen saturation, once the PID processed SQ value exceeds the threshold, indicating that the measured value is reliable and accurate, the device makes the decision to display the oxygen saturation value on its display monitor. The measured value (i.e., oxygen saturation) remains displayed until the PIE processed SQ value drops below a threshold.

On the other hand, if the PID processed value is below the threshold (step 216), the measured physiologic value is not displayed. Next, the PID processed SQ value is compared to another threshold (step 220). The threshold at step 220 may be equal to the threshold at step 216. Alternately the threshold at step 220 may be set to a different value if the PID processed SQ value exceeds the second threshold value, the decision loop is ended (step 224) and the process begins all over again (step 210). On the other hand, if the PID processed SQ value is lower than the second threshold, a diagnostic message is displayed (step 226) on the medical devices display monitor to appropriately guide the clinician. For example, a text message such as "ADJUST SENSOR" is posted on the display monitor to guide the clinician to adjust the sensor's positioning. Once the "ADJUST SENSOR" text message is displayed, it remains displayed until the sensor's location is adjusted. Alternately, the diagnostic message may be an audible or visual alarm indicating that the sensor location must be adjusted.

While the PIED processing of the SQ value provides the advantages described above, it may lead to a delayed response, for example a PID processed SQ value with a large integral component- due to the required integration times. To avoid a potential delayed response, the PID algorithm is adjusted to reduce the significance of the integral component. Alternately, the algorithms are configured to base the decision making on a non-PID processed SQ signal.

Experiments conducted by the inventors show that pulse oximeter devices configured to use embodiments of the present invention described above, provide an increase in the overall posting time of the measures physiological values. Further, the improvements related to implementation of the embodiments of the present invention, provide for improvements in the accuracy of the displayed saturation values. Additionally, the "ADJUST SENSOR" feature leads to improved sensor placement. And lastly, with improved sensor placement, posting of the displayed signal begins sooner.

As will be understood by those of skill in the art, the present invention which is related to estimating the reliability and accuracy of a monitored value, and diagnostics algorithms based on that estimate, may be embodied in other specific forms without departing from the essential characteristics thereof. For example, variables other than oxygen saturation such as pulse rate, blood pressure, temperature, or any other physiological variable could be continuously or periodically tracked. Further, while the present embodiments have been described in the time-domain, frequency-based methods are equally relevant to the embodiments of the present invention. Accordingly, the foregoing disclosure is intended to be illustrative, but not limiting, of the scope of the invention which is set forth in the following claims.

The invention claimed is:

1. A method for evaluating a signal, comprising:
periodically calculating, during continuous measurement of a measured signal, a signal quality metric by combining two or more signal quality indicators, wherein each signal quality indicator is a different type of measured parameter;
comparing the signal quality metric or a value derived from the signal quality metric to a first threshold;
if the first threshold is exceeded, displaying a value of a physiological parameter derived from the measured signal;
comparing the same signal quality metric or value derived from the signal quality metric to a second threshold if the processed signal quality metric is less than the first threshold; and
providing an indication of poor signal quality if the signal quality metric or the value derived from the signal quality metric is less than the first threshold and the second threshold.

2. The method, as set forth by claim 1, wherein the signal quality indicators comprise a similarity overlap between a first and a second electromagnetic signal, wherein the first and second electromagnetic signals differ in frequency.

3. The method, as set forth by claim 1, wherein the signal quality indicators comprise a measure based on a shape of an arterial pulse.

4. The method, as set forth by claim 1, wherein the signal quality indicators comprise a frequency content of a pulse waveform relative to pulse rate.

5. The method, as set forth by claim 1, wherein the value derived from the quality metric comprises a PID processed signal quality metric derived by operating on the signal quality metric using a combination of proportional (P), integral (I), and derivative (D) control operations.

6. The method, as set forth by claim 1, wherein the indication comprises a text message indicating the poor signal quality.

7. The method, as set forth by claim 1, wherein the indication comprises an alarm indicating the poor signal quality.

8. A method for evaluating a physiological measurement, comprising the acts of:
periodically calculating a signal quality metric based on a physiological parameter acquired by a physiological sensor, wherein the periodic calculation is performed during an ongoing measurement of the physiological parameter;
displaying a current value of the physiological parameter if the signal quality metric or a value derived from the signal quality metric exceeds a first threshold;
if the first threshold is not exceeded, comparing the same signal quality metric or value derived from the signal quality metric to a second threshold; and
directing an operator to reposition the physiological sensor if the second threshold value is not exceeded.

9. The method, as set forth by claim 8, wherein the physiological parameter and the two or more types of signal quality indicators are measured using a pulse oximetry sensor.

10. The method, as set forth by claim 8, wherein the value derived from the quality metric comprises a PID processed signal quality metric derived by operating on the signal quality metric using a combination of proportional (P), integral (I), or derivative (D) control operations.

11. The method, as set forth by claim 8, wherein directing the operator comprises providing one or more of a visual, audible, or temporal indication of signal quality.

12. The method, as set forth by claim 8, wherein the signal quality metric corresponds to dislocations of the sensor.

13. A non-transitory machine readable medium comprising executable code which, when executed:
periodically calculates, during an ongoing measurement of a physiological parameter, a signal quality metric by combining two or more signal quality indicators, wherein each signal quality indicator is a different type of measured parameter;
compares the signal quality metric or a value derived from the signal quality metric to a first threshold;
displays a value of the physiological parameter if the first threshold is exceeded;
compares the same signal quality metric or value derived from the signal quality metric to a second threshold if the first threshold is not exceeded; and
provides an indication of poor signal quality if the second threshold is not exceeded.

14. The non-transitory machine readable medium, as set forth by claim 13, wherein the code, when executed, measures one type of signal quality indicator based on the shape of an arterial pulse.

15. The non-transitory machine readable medium, as set forth by claim 13, wherein the code, when executed, obtains a frequency content of a pulse waveform relative to pulse rate as one type of signal quality indicators.

16. The non-transitory machine readable medium, as set forth by claim 13, wherein the value derived from the signal quality metric is derived using a combination of proportional (P), integral (I), and derivative (D) control operations.

17. A non-transitory machine readable medium comprising executable code which, when executed:
periodically calculates a signal quality metric based on a physiological parameter acquired by a physiological sensor, wherein the periodic calculation is performed during a continuous measurement of the physiological parameter;
displays a current value of the physiological parameter if the signal quality metric or a value derived from the signal quality metric exceeds a first threshold;
compares the same signal quality metric or value derived from the signal quality metric to a second threshold if the first threshold is not exceeded; and
directs an operator to reposition the physiological sensor if the second threshold value is not exceeded.

18. The non-transitory machine readable medium, as set forth by claim 17, wherein the value derived from the signal quality metric is derived using a combination of proportional (P), integral (I), or derivative (D) control operations.

19. The non-transitory machine readable medium, as set forth by claim 17, wherein the code, when executed, provides one or more of a visual, audible, or temporal indication of signal quality.

20. A system for evaluating a signal comprising:
a sensor adapted to measure a physiological parameter and two or more types of signal quality indicators indicative of the reliability and accuracy of the measurement of the physiological parameter;
a signal processor adapted to periodically calculate, during continuous measurement of the physiological parameter, a signal quality metric by combining the two or more types of signal quality indicators, to compare the signal quality metric or a value derived from the signal quality metric to a first threshold, to display a value of the physiological parameter if the first threshold is exceeded, to compare the same signal quality metric or value derived from the signal quality metric to a second threshold if the first threshold is not exceeded, and to provide an indication of poor signal quality if the second threshold is not exceeded; and
a device adapted to display or play the indication of poor signal quality.

21. The system, as set forth by claim 20, wherein the sensor is a pulse oximetry sensor.

22. The system, as set forth by claim 20, wherein the signal processor calculates the value derived from the signal quality metric as a combination of proportional (P), integral (I), and derivative (D) control operations.

23. The system, as set forth by claim 20, wherein the device is a monitor.

24. The system, as set forth by claim 20, wherein the device is an audio playback device.

25. A system for evaluating a physiological measurement, comprising:
a sensor adapted to measure a physiological parameter and two or more types of signal quality indicators indicative of the reliability and accuracy of the measurement of the physiological parameter;
a signal processor adapted to periodically calculate, during ongoing measurement of the physiological parameter, a signal quality metric by combining the two or more types of signal quality indicators, to display a current value of the physiological measurement if the signal quality metric or a value derived from the signal quality metric exceeds a first threshold, to compare the same signal quality metric or value derived from the signal quality metric to a second threshold value if the first threshold is not exceeded, and to direct an operator to reposition the physiological sensor if the second threshold value is not exceeded; and
an interface device configured to provide the direction to the operator.

26. The system, as set forth by claim 25, wherein the interface device comprises at least one of a display or a speaker.

27. A method for evaluating a signal comprising:
measuring two or more types of signal quality indicators associated with the signal obtained from a measurement of a physiological parameter;
periodically calculating, during ongoing measurement of the signal, a signal quality metric based on a combination of the two or more types of signal quality indicators;
generating a processed signal quality metric based on the signal quality metric;
comparing the processed signal quality metric to a first threshold;
if the first threshold is exceeded, displaying a value of the physiological parameter;
if the first threshold is not exceeded, comparing the processed signal quality metric to a second threshold; and
if a second threshold is not exceeded, providing one or both of an indication of poor signal quality or an indication that a physiological sensor should be moved.

* * * * *